United States Patent [19]
Rodgers et al.

[11] Patent Number: 5,478,837
[45] Date of Patent: Dec. 26, 1995

[54] USE OF QUINACRINE IN PREVENTING ADHESION FORMATION

[75] Inventors: Kathleen E. Rodgers, Long Beach; Gere S. Dizerega, Pasadena, both of Calif.

[73] Assignee: University of Southern California, Los Angeles, Calif.

[21] Appl. No.: 253,438

[22] Filed: Jun. 7, 1994

[51] Int. Cl.$^6$ ..................................... A61K 31/44
[52] U.S. Cl. .................. 514/297; 424/450; 424/486; 424/488; 424/491; 424/492; 424/497; 424/499; 546/106
[58] Field of Search ..................... 514/297; 546/106; 424/450, 486, 488, 491, 492, 497, 499

[56] References Cited

U.S. PATENT DOCUMENTS

| | | | |
|---|---|---|---|
| 4,158,050 | 6/1979 | Zipper | 514/297 |
| 4,181,725 | 1/1980 | Voorhees et al. | 514/297 |
| 4,185,618 | 1/1980 | Corey | 514/297 |
| 4,937,254 | 6/1990 | Sheffield et al. | |

OTHER PUBLICATIONS diZerega, G. S. & Rodgers, K. E., "Prevention of Postoperative Adhesions," in *The Peritoneum*, diZerega, G. S. & Rodgers, K. E., eds., Springer–Verlag, New York, pp. 307–369 (1992).

Elkins, T. E., "Can a Pro–Coagulant Substance Prevent Adhesions?" in *Treatment of Post–Surgical Adhesions*, diZerega, G. S. et al., eds., Wiley–Liss, New York, pp. 103–112 (1990).

Rodgers, K. E., "Nonsteroidal anti–inflammatory drugs (NSAIDs) in the treatment of Postsurgical adhesion," in *Treatment of Post–Surgical Adhesions*, diZerega, G. S. et al., eds., Wiley–Liss, New York, pp. 119–129 (1990).

Moreno, J. J. et al., "PLA$_2$–induced oedema in rat skin and histamine release in rat mast cells. Evidence for involvement of lysophospholipids in the mechanism of action," *Agents Actions* 36, 258 (1992).

Prowse, C. et al., "Prevention of the platelet alpha–granule release reaction by membrane–active drugs," *Thrombosis Research* 25, 219 (1982).

Janzing, et al., "Intrapleural quinacrine instillation for recurrent pneumothorax or persistent air leak," *Ann. Thoracic Surgery* 55, 368 (1993).

Senior et al., "Morphometric and kinetic studies on the change induced in the intestinal mucosa of rats by intraperitoneal administration of quinacrine," *Cell & Tissue Kinetics* 17, 445 (1984).

Struhar, D. et al., "Quinacrine inhibits oxygen radicals release from human alveolar macrophages," *Int. J. Immunopharmac.* 14, 275 (1992).

Foeldes–Filep, E. & Filep, J. G., "Mepacrine inhibits fMLP–induced activation of human neutrophil granulocytes, leukotriene B$_4$ formation, and fMLP binding," *J. Leukocyte Biol.* 52, 545 (1992).

Rodgers, K. et al., "Effects of tolmetin sodium dihydrate on normal and postsurgical peritoneal cell function," *Int. J. Immunopharmac.* 10, 111 (1988).

Agrenius, V. et al., "Pleural fibrinolytic activity is decreased in inflammation as demonstrated in quinacrine pleurodesis treatment of malignant pleural effusion," *Am. Rev. Respir. Dis.* 140, 1381 (1989).

Suzuki, A. et al., "Participation of phospholipase A$_2$ in induction of tissue plasminogen activator (t–PA) production by human fibroblast, IMR–90 cells, stimulated by proteose peptone," *Thromb. Res.* 64, 191 (1991).

Mumford, S. D. & Kiesel, E., "Sterilization needs in the 1990s: The case for quinacrine nonsurgical female sterilization," *Am. J. Obstet. Gynecol.* 167, 1203 (1992).

Lennartz, M. R. & Brown, E. J., "Arachidonic acid is essential for IgG Fc receptor–mediated phagocytosis by human monocytes," *J. Immunol.* 147, 621 (1991).

Kim, T. K. et al., "Extended–release formulation of morphine for subcutaneous administration," *Cancer Chemother. Pharmacol.* 33, 187 (1993).

Chatelut, E. et al., "A slow–release methotrexate formulation for intrathecal chemotherapy," *Cancer Chemother. Pharmacol.* 32, 179 (1993).

Lewis, D. H., "Controlled Release of Bioactive Agents from Lactide/Glycolide Polymers," in *Biodegradable polymers as drug delivery systems*, Jason & Langer, eds., pp. 1–41 (1990).

Hoeckel, M. et al., "Prevention of Peritoneal Adhesions in the Rat with Sustained Intraperitoneal Dexamethasone Deliverd by a Novel Therapeutic System," *Annales Chirurgiae et Gynaecologiae* 76:306–313 (1987).

Rodgers, K. et al., "Inhibition of Postsurgical Adhesions by Liposomes Containing Nonsteroidal Antiinflammatory Drugs," *Int. J. Fertil.* 35:40 (1990).

Abe, H. et al., "The Effect of Intraperitoneal Administration of Sodium Tolmetin–Hyaluronic Acid on the Postsurgical Cell Infiltration In Vivo," *J. Surg. Res.* 49:322 (1990).

Diamond, M. P. et al., "Synergistic effects of Interceed(TC7) and heparin in reducing adhesion formation in the rabbit uterine horn model," *Fertility and Sterility* 55, 389 (1991).

Diamond, M. P. et al., "Adhesion reformation: reduction by the use of Interceed(TC7) plus heparin," *J. Gynecologic Surg.* 7, 1 (1991).

Nishimura, K. et al., "The use of ibuprofen for the prevention of postoperative adhesions in rabbits," *Am. J. Med.* 77:102–6 (1984).

Interceed (TC7) Adhesion Barrier Study Group, "Prevention of Postsurgical adhesions by Interceed (TC7), an Absorbable Adhesion Barrier: A Prospective, Randomized Multicenter Clinical Study", *Fertility and Sterility*, 51:933 (1989).

Bjoerkman, S. et al., "Pharmacokinetics of Quinacrine after Intrapleural Instillation in Rabbits and Man", *J. Pharm. Pharmacol.*, 41:160–163 (1988).

Beckman, S. et al., "Possible Involvement of Phospholipase Activation in Erythroid Progenitor Cell Proliferation", *Exp. Hematol.*, 17:309–312 (1989).

*Primary Examiner*—Glennon H. Hollrah
*Assistant Examiner*—Scott C. Rand
*Attorney, Agent, or Firm*—Robbins Berliner & Carson

[57] ABSTRACT

Compositions and methods for prevention of adhesion formation, whereby an effective amount of quinacrine as active agent is administered for a period of time sufficient to permit tissue repair. The active agent is preferably administered in conjunction with a delivery vehicle (e.g., microcapsules, microspheres, lipid-based systems, viscous instillates and absorbable mechanical barriers) useful for maintaining local concentrations of the compound at an effective level.

15 Claims, No Drawings

USE OF QUINACRINE IN PREVENTING ADHESION FORMATION

BACKGROUND OF THE INVENTION

The present invention relates to the medical arts. In particular, the present invention is directed to compositions and methods for use in preventing the formation of postoperative adhesions.

Adhesion formation, in particular following peritoneal surgery, is a major source of postoperative morbidity and mortality. Appendectomy and gynecologic surgery are the most frequent surgical procedures implicated in clinically significant adhesion formation. The most serious complication of intraperitoneal adhesions is intestinal obstruction; in addition, adhesions are associated with chronic or recurrent pelvic pain and infertility in females.

The pathogenesis of adhesion formation between organ surfaces is complex and not entirely understood. The first step is believed to involve excess fibrin deposition to form a scaffold. Organization of the fibrin scaffold by cellular elements, including fibroblasts and mesothelial cells, then follows. Notwithstanding a lack of understanding of all of the mechanisms underlying the formation of intraperitoneal adhesions, it is clear that substantially more is involved in the process than simple mechanisms of cell to cell adhesion; moreover, agents which are known to prevent the adhesion of one cell to another do not necessarily have utility in preventing the formation of intraperitoneal adhesions.

Various approaches for the prevention of adhesion formation have been actively explored [diZerega, G. S. & Rodgers, K. E., "Prevention of Postoperative Adhesions," in *The Peritoneum*, diZerega, G. S. & Rodgers, K. E., eds., Springer-Verlag, New York, pp.307–369 (1992)]. In general, the treatments fall into three categories: prevention of fibrin deposition in the peritoneal exudate; reduction of local tissue inflammation; and removal of fibrin deposits.

Therapeutic attempts to prevent fibrin deposition include peritoneal lavages to dilute or wash away fibrinous exudate, surgical techniques to minimize tissue ischemia and introduction of barriers to limit apposition of healing serosal surfaces. Although the use of agents affecting coagulation of the fibrinous fluid has also been proposed, results obtained to date suggest that the use of procoagulants in areas of substantial bleeding may actually promote adhesion formation [Elkins, T. E., "Can a Pro-Coagulant Substance Prevent Adhesions"? in *Treatment of Post-Surgical Adhesions*, diZerega, G. S. et al., eds., Wiley,Liss, New York, pp. 103–112 (1990)].

Physical barriers have been used in attempts to prevent adhesion formation by limiting tissue apposition during the critical period of peritoneal healing, thereby minimizing the development of fibrin matrix between tissue surfaces. Barrier agents which have been employed include both mechanical barriers and viscous solutions. Mixed results have been obtained using a barrier comprising a thin sheet of expanded polytetrafluoroethylene; in any event, such a membrane is less than ideal, as it must be sutured into place and is nonabsorbable. While an absorbable barrier (for example, a barrier made of oxidized regenerated cellulose) would be preferable, not all studies have demonstrated the efficacy of such barriers in preventing adhesions. Liquid barriers have also been considered for use in preventing adhesions; for example, chondroitin sulfate and carboxymethyl cellulose have both shown some promise in animal models. In addition, solutions of dextran 70 (molecular weight=70,000) have been the subject of a number of clinical studies. Not all clinical evaluations of 32% dextran 70 have found a therapeutic effect, however, and the clinical use of the solution is also associated with clinically important side effects.

Anti-inflammatory drugs have been evaluated for their effects on postoperative adhesion formation, as they may limit the release of fibrinous exudate in response to inflammation at the surgical site. Two general classes of these drugs were tested: corticosteroids and nonsteroidal anti-inflammatory drugs. The results of corticosteroid use in animal studies have generally not been encouraging, and clinical use of corticosteroids is limited by their other pharmacologic properties. While experimental evaluations of nonsteroidal anti-inflammatory drugs in postoperative adhesion formation show promise [Rodgers, K. E., "Nonsteroidal anti-inflammatory drugs (NSAIDs) in the treatment of Postsurgical adhesion," in *Treatment of Post-Surgical Adhesions*, diZerega, G. S. et al., eds., Wiley-Liss, New York, pp. 119–129 (1990)], clinical evaluations of these drugs for adhesion prevention is needed.

The third approach explored to date involves the removal of fibrin deposits. Although proteolytic enzymes (e.g., pepsin, trypsin and papain) should theoretically augment the local fibrinolytic system and limit adhesion formation, these enzymes are rapidly neutralized by peritoneal exudates rendering them virtually useless for adhesion prophylaxis. While various fibrinolytics (for example, fibrinolysin, streptokinase and urokinase) have been advocated, a potential complication to the clinical use of these enzymes in postoperative therapy is excessive bleeding resulting from their administration. Topical application of a recombinant tissue plasminogen activator (rt-PA) has been shown to reduce adhesion formation in a variety of animal models; further research is necessary to develop suitable delivery systems to provide this drug to the surgical site and identify the postoperative time when adhesion prevention is feasible.

To date, no single therapeutic approach has proven universally effective in preventing formation of postoperative intraperitoneal adhesions. Therefore, there is a need for compositions and methods which may be used safely and effectively to prevent adhesion formation in a variety of different contexts.

It is an object of the present invention to provide compositions and methods for the minimization or prevention of post-surgical adhesion formation.

SUMMARY OF THE INVENTION

In accordance with one aspect of the present invention, adhesion formation is minimized or prevented by administration of an effective amount of quinacrine at a site of potential adhesion formation for a period of time sufficient to permit substantial tissue repair (e.g., re-epithelialization or mesothelial repair) at the site. Pursuant to another aspect of the present invention, there is provided a composition for the minimization or prevention of adhesion formation comprising quinacrine and a drug delivery system which maintains an effective concentration of the compound at a site of potential adhesion formation during the perioperative interval.

DETAILED DESCRIPTION OF THE INVENTION

The inventive compositions and methods are useful in minimizing or preventing adhesion formation, the most common cause of which is prior surgery. The inventive compositions and methods have been shown to be especially effective in preventing the formation of adhesions between organ surfaces, in particular adhesion formation in the peritoneum following surgery. In addition, the present invention finds utility in other contexts, e.g., for cardiovascular, orthopedic, thoracic, ophthalmic, CNS and other uses, where prevention of the formation of adhesions is a significant concern. For example, prevention of adhesion formation or drug loculation during the intraperitoneal administration of other chemotherapeutic agents is contemplated as within the scope of the present invention. For the purposes of the following discussion, attention is directed primarily to description of compositions and methods useful in inhibiting peritoneal adhesion formation.

The present invention contemplates the use of quinacrine (most commonly described in the literature in the form of its hydrochloride salt). Quinacrine hydrochloride is described by the following formulas: $N^6$-(6-chloro-2-methoxy-9-acridinyl)-$N^1$, $N^1$-diethyl-1,4-pentanediamine dihydrochloride; 6-chloro-9-[[4-(diethylamino)- 1-methylbutyl]amino]-2-methoxyacridine dihydrochloride; and 3-chloro-7-methoxy-9-( 1-methyl-4-diethyl aminobutylamino)acridine dihydrochloride. It is available in formulations for pharmaceutical use under a number of trade designations, including Atabrine$^R$ Hydrochloride (Sanofi Winthrop Pharmaceuticals, New York, N.Y.).

Clinically, quinacrine hydrochloride is employed for the treatment of giardiasis and cestodiasis. In addition, it has been used for the treatment and suppression of malaria. Quinacrine hydrochloride has been reported to be a phospholipase $A_2$ (PLA$_2$) inhibitor in platelets [Beckman, B. S. & Seferynska, I., "Possible involvement of phospholipase activation in erythroid progenitor cell proliferation," *Exp. Hematol.* 17, 309 (1989)]. Coinjection of quinacrine hydrochloride with PLA$_2$ reduced the inflammogenic potency of the latter by 64%, suggesting that quinacrine hydrochloride might have some anti-inflammatory activity [Moreno, J. J. et al., "PLA$_2$-induced oedema in rat skin and histamine release in rat mast cells. Evidence for involvement of lysophospholipids in the mechanism of action," *Agents Actions* 36, 258 (1992)]. In addition, quinacrine has been found to prevent the alpha-granule release reaction of platelets [Prowse, C. et al., "Prevention of the platelet alpha-granule release reaction by membrane-active drugs," *Thrombosis Research* 25, 219 (1982)].

In clinical practice, quinacrine has been used for pleurodesis through intrapleural administration. When the material was administered at 100 mg/day in 50 ml saline for 4 days, the peak concentration reported was less than 10 ng/ml (Janzing, et al., "Intrapleural quinacrine instillation for recurrent pneumothorax or persistent air leak," *Ann. Thoracic Surgery* 55, 368 (1993)]. The intraperitoneal toxicity of quinacrine in rats has also been examined [Senoir et al., "Morphometric and kinetic studies on the change induced in the intestinal mucosa of rats by intraperitoneal administration of quinacrine," *Cell & Tissue Kinetics* 17, 445 (1984)]; in these animals, 12 mg (equivalent to 48 mg/kg) was given to rats each day for 4 days, for a total of 192 mg/kg.

While the present invention is not bound to any particular theory, it is believed that quinacrine may inhibit adhesion formation through a variety of mechanisms. Quinacrine acts to inhibit platelet aggregation (which in turn inhibits the release of alpha granules) through inhibition of PLA$_2$. Inhibition of platelet aggregation results in a reduction in fibrin deposition; this contributes to a reduced rate of peritoneal adhesion formation. In addition, reduction of PLA$_2$ reduces the amount of arachidonic acid released. Arachidonic acid is metabolized to inflammatory mediators through various enzymes. Therefore, quinacrine has an anti-inflammatory activity through inhibition of PLA$_2$. Exposure of leukocytes to quinacrine leads to a reduction of respiratory burst activity and the secretion of leukotrienes.

As is well recognized in the art, however, no one of these possible mechanisms of action of quinacrine would in and of itself be sufficient to enable one to predict whether this compound would have any utility in reduction of adhesion formation.

For example, quinacrine has been found to have an inhibitory effect on oxygen radicals secreted by alveolar macrophages [Struhar, D. et al., "Quinacrine inhibits oxygen radicals release from human alveolar macrophages," *Int. J. Immunopharmac.* 14, 275 (1992)] and on superoxide production by polymorphonuclear leukocytes [Foeldes-Filep, E. & Filep, J. G., "Mepacrine inhibits fMLP-induced activation of human neutrophil granulocytes, leukotriene $B_4$ formation, and fMLP binding," *J. Leukocyte Biol.* 52, 545 (1992)]. In contrast, tolmetin (an agent also shown to reduce adhesion formation) has been shown to increase the production of oxygen radicals by postoperative macrophages [Rodgers, K. et al., "Effects of tolmetin sodium dihydrate on normal and postsurgical peritoneal cell function," *Int. J. Immunopharmac.* 10, 111 (1988)].

In addition, intrapleural administration of quinacrine has been reported to cause an inflammatory response, with increased coagulation and decreased fibrinolysis (which would prolong fibrin deposition and increase the scaffold for adhesion formation); this is believed to be a result of an increase in plasminogen activator inhibitor (PAI-1) levels [Agrenius, V. et al., "Increased coagulation activity of the pleura after tube drainage and quinacrine instillation in malignant pleural effusion," *Eur. Respir. J.* 4, 11.35 (1991); Agrenius, V. et al., "Pleural fibrinolytic activity is decreased in inflammation as demonstrated in quinacrine pleurodesis treatment of malignant pleural effusion," *Am. Rev. Respir. Dis.* 140, 1381 (1989)] and a decrease in tissue plasminogen activator (t-PA) levels [Suzuki, A. et al., "Participation of phospholipase $A_2$ in induction of tissue plasminogen activator (t-PA) production by human fibroblast, IMR-90 cells, stimulated by proteose peptone," *Thromb. Res.* 64, 191 (1991)]. Further, 252 mg quinacrine pellets have been used to cause nonsurgical sterilization through occlusion of fallopian tubes by fibrosis and inflammation after transcervical intrauterine administration [Mumford, S. D. & Kessel, E., "Sterilization needs in the 1990s: The case for quinacrine nonsurgical female sterilization," *Am. J. Obstet. Gynecol.* 167, 1203 (1992)]. A compound having such an activity profile would clearly not be expected to have utility in prevention of adhesion formation.

Finally, quinacrine causes a decrease in phagocytosis [Lennartz, M. R. & Brown, E. J., "Arachidonic acid is essential for IgG Fc receptor-mediated phagocytosis by human monocytes," *J. Immunol.* 147, 621 ( 1991)]. In contrast, tolmetin increases phagocytosis [Rodgers, K. et al. (1988), supra].

Pursuant to the method of the present invention, quinacrine is maintained in an effective concentration at the site of potential adhesion formation for a period of time sufficient to permit substantial re-epithelialization. The active agent is typically administered over the perioperative interval, which for purposes of the present invention may include time shortly prior to surgery through the surgery itself up to some time after completion of surgery. The term of administration may vary depending upon a number of factors which would be readily appreciated by those skilled in the art. In general, administration of a composition in accordance with the present invention should be effected from the time of surgery for at least 24 to 48 hours after completion of the surgical procedure. As healing is in most cases complete within about two weeks, it is generally not necessary to continue administration of a composition in accordance with the present invention much longer than two weeks. Preferably, a composition in accordance with the present invention is administered from about the time of surgery for a period of about 24 hours to about 7 days.

The rate of administration of quinacrine may be varied over a fairly broad range. The concentrations of quinacrine which can be administered would be limited by efficacy at the lower end and the solubility of the compound at the upper end.

In the model systems employed in the examples reported herein, quinacrine was shown to reduce the incidence of peritoneal adhesions at concentrations of about 5 mg/ml to about 0.056 mg/ml with continuous release throughout the postsurgical interval using an Alzet miniosmotic pump at a rate of 10 μl/hour. Local concentrations on the order of about 0.000001 μg/ml to about 28 mg/ml, and preferably about 0.0001 μg/ml to about 5 mg/ml, would be appropriate. At the maximum concentration, this would correspond to about 19 mg/kg quinacrine over a 7-day period of time. Based upon the weight of a typical human patient, this would correspond to a range of 0.000106 pg/cm$^2$/hr to 2.97 μg/cm$^2$/hr or 0.0000424 pg/cm$^2$/hr/kg to 1.19 μg/cm$^2$/hr/kg; the preferred range is 0.0106 pg/cm$^2$/hr to 0.53 μg/cm$^2$/hr or 0.00424 pg/cm$^2$/hr/kg to 0.212 μg/cm$^2$/hr/kg.

The active agent may be administered directly in a suitable vehicle, for example phosphate-buffered saline (PBS). Pursuant to preferred embodiments of the present invention, however, the active agent is administered in a single dose delivery (for example, prior to suturing after surgery) using a drug-delivery system which enables the maintenance of requisite concentrations of the compound for a period of time sufficient for re-epithelialization. A suitable drug-delivery system would itself be essentially non-inflammatory and non-immunogenic; in addition, it would permit release of quinacrine so as to maintain effective levels thereof over the desired time period. A large variety of alternatives are known in the art as suitable for purposes of sustained release and are contemplated as within the scope of the present invention. Suitable delivery vehicles include, but are not limited to, the following: microcapsules or microspheres; liposomes and other lipid-based release systems, such as DepoFoam extended-release formulations comprising spherical particles bounded by a single bilayer lipid membrane and each containing numerous nonconcentric aqueous chambers which encapsulate the active ingredient [see, e.g., Kim, T. K. et al., "Extended-release formulation of morphine for subcutaneous administration," *Cancer Chemother. Pharmacol.* 33, 187 (1993); Chatelut, E. et al., "A slow-release methotrexate formulation for intrathecal chemotherapy," *Cancer Chemother. Pharmacol.* 32, 179 (1993)]; viscous instillates; absorbable and/or biodegradable mechanical barriers; and polymeric delivery materials, such as polyethylene oxide/polypropylene oxide block copolymers (e.g.,poloxamers), poly-orthoesters, cross-linked polyvinyl alcohol, polyanhydrides, polymethacrylate and polymethacrylamide hydrogels, anionic carbohydrate polymers, etc. Useful delivery systems are well known in the art and are described in, e.g., U.S. Pat. No. 4,937,254 to Sheffield et al., the entire disclosure of which is hereby incorporated by reference.

One particularly suitable formulation to achieve the desired near zero-order release of quinacrine comprises injectable microcapsules or microspheres prepared from a biodegradable polymer, such as poly(dl-lactide), poly(dl-lactide-co-glycolide), polycaprolactone, polyglycolide, polylactic acid-co-glycolide, poly(hydroxybutyric acid), a polyortho-ester or a polyacetal. Injectable systems comprising microcapsules or microspheres of a diameter on the order of about 50 to about 500 μm offer advantages over other delivery systems. For example, they generally use less active agent and may be administered by paramedical personnel. Moreover, such systems are inherently flexible in the design of the duration and rate of separate drug release by selection of microcapsule size, drug loading and dosage administered. In addition, such microcapsules can be successfully sterilized with gamma irradiation. Of course, these biodegradable polymers (such as lactide and caprolactone polymers) may alternatively be used in formulations other than microcapsules or microspheres; for example, pre-made films and spray-on films of these polymers containing the active agent would be suitable for use in accordance with the present invention.

Microcapsules are systems comprising a polymeric wall that encloses a liquid or solid core. The capsule wall usually does not react with the core material; however, it is designed to provide sufficient strength to enable normal handling without rupture while being sufficiently thin to allow a high core to wall volume ratio. The capsule contents remain within the wall until released by diffusion or other means that dissolve, melt, break, rupture or remove the capsule material. Preferably, the capsule wall can be made to degrade and decompose in suitable environments while diffusing the core material through the capsule wall to allow for its slow, prolonged delivery.

The mechanism of release in biodegradable microcapsules is a combination of drug diffusion and polymer biodegradation. Therefore, the rate and duration of release are determined by microcapsule size, drug content and quality, and polymer parameters such as crystallinity, molecular weight and composition. In particular, adjustment in the amount of drug released is generally achieved by modification of capsule wall thickness, capsule diameter, or both. Detailed information concerning the design, preparation and use of microspheres and microcapsules is provided by, e.g., Lewis, D. H., "Controlled Release of Bioactive Agents from Lactide/Glycolide Polymers," in *Biodegradable polymers as drug delivery systems*, Jason & Langer, eds., pp. 1–41 (1990), the entire disclosure of which is hereby incorporated by reference. The sustained intraperitoneal release of an active agent (dexamethasone) using poly(lactide-co-glycolide) microparticles is described in Hoeckel, M. et al., "Prevention of Peritoneal Adhesions in the Rat with Sustained Intraperitoneal Dexamethasone Delivered by a Novel Therapeutic System," *Annales Chirurgiae et Gynaecologiae* 76:306–313 (1987), the entire disclosure of which is also incorporated by reference.

As is well known to those skilled in the art, various methods are currently available for preparing microcapsules, any of which could be employed to provide formulations in accordance with the present invention. Biodegradable polymeric materials suitable for preparation of microcapsules for controlled (i.e., near zero-order) release would be readily determined through routine experimentation by those skilled in the art. Moreover, alternative delivery systems suitable for use in accordance with the present invention (for example, fibers or filaments comprising the active agents) based on biodegradable polymers are also contemplated as within the scope of the present invention.

An alternative approach for the single-dose delivery of quinacrine in accordance with the present invention involves the use of liposomes. The encapsulation of an active agent in multilamellar vesicles (or liposomes) is a well known technique to assist in target drug delivery and prolong drug residence. In a typical procedure, a liposome-forming powdered lipid mixture is added to the desired quantity of active agent in aqueous solution (e.g., phosphate-buffered saline) to form a suspension. After a suitable hydration period, the hydrated suspension is then autoclaved to provide the liposome-active agent preparations. A lipid mixture suitable for formation of liposomes may be prepared from L-alpha-distearoyl phosphatidylcholine and cholesterol dissolved in chloroform, to which alpha-tocopherol is added; other compositions and methods for formation of liposomes would, however, also be useful for this purpose. The intraperitoneal administration of liposomes containing ibuprofen or tolmetin is described in Rodgers, K. et al., "Inhibition of Postsurgical Adhesions by Liposomes Containing Nonsteroidal Antiinflammatory Drugs," *Int. J. Fertil.* 35:40 (1990), the entire disclosure of which is hereby incorporated by reference.

Yet another suitable approach for single dose delivery of quinacrine in accordance with the present invention involves the use of so-called viscous instillates. In this technique, high-molecular-weight carriers are used in admixture with the active agents, giving rise to an extended structure which produces a solution with high viscosity. Suitable high-molecular-weight carriers include, but are not limited to, the following: dextrans and cyclodextrans; hydrogels; cross-linked viscous materials, including viscoelastics and cross-linked viscoelastics; carboxymethylcellulose; hyaluronic acid; and chondroitin sulfate. While some studies have suggested that the use of viscous barrier solutions per se may have an advantageous effect in reducing the incidence of adhesion formation, it is believed that any such effect is of limited scope when compared to the combination of quinacrine and carrier. The intraperitoneal administration of a viscous instillate comprising tolmetin is described in Abe, H. et al., "The Effect of Intraperitoneal Administration of Sodium Tolmetin-Hyaluronic Acid on the Postsurgical Cell Infiltration In Vivo," *J. Surg. Res.* 49:322 (1990), the entire disclosure of which is hereby incorporated by reference.

Pursuant to yet another approach, quinacrine is administered in combination with an absorbable mechanical barrier which alone reduces adhesion formation. As would be readily apparent to one working in the field, quinacrine may be covalently or non-covalently (e.g., ionically) bound to such a barrier, or it may simply be dispersed therein. A particularly suitable mechanical barrier for use in this particular embodiment of the invention comprises oxidized regenerated cellulose; one such absorbable barrier is available under the designation INTERCEED(TC7) from Johnson and Johnson Medical, Inc., New Brunswick, N.J. [INTERCEED(TC7) Adhesion Barrier Study Group, "Prevention of postsurgical adhesions by INTERCEED(TC7), an absorbable adhesion barrier: a prospective, randomized multicenter clinical study," *Fertility and Sterility* 51, 933 (1989)]. The use of a mechanical barrier as a carrier to deliver heparin to traumatized surfaces is disclosed in Diamond, M. P. et al., "Synergistic effects of INTERCEED(TC7) and heparin in reducing adhesion formation in the rabbit uterine horn model," *Fertility and Sterility* 55, 389 (1991) and Diamond, M. P. et al., "Adhesion reformation: reduction by the use of Interceed(TC7) plus heparin," *J. Gynecologic Surg.* 7, 1 (1991), the entire disclosures of which are hereby incorporated by reference.

The invention may be better understood with reference to the accompanying examples, which are intended to be illustrative only and should not be viewed as in any sense limiting the scope of the invention, which is defined hereinafter in the accompanying claims.

EXAMPLES

Multiple studies to confirm the efficacy of quinacrine in the reduction of adhesion formation after peritoneal surgery were performed. Two model systems were employed: the sidewall adhesion model and the uterine horn model. A clear correlation between results obtained using both of these models and utility in adhesion prevention has been demonstrated with INTERCEED(TC7), for which clear clinical efficacy has been shown and FDA approval for adhesion prevention in gynecological surgery has been obtained.

In the peritoneal sidewall model, rabbit were pre-anesthetized with 1.2 mg/kg acetylpromazine and anesthetized with a mixture of 55 mg/kg ketamine hydrochloride and 5 mg/kg xylazine intramuscularly. Following preparation for sterile surgery, a midline laparotomy was performed. A 3×3-cm area of peritoneum and transversus abdominis muscle was removed on the right lateral abdominal wall. Electrocautery was used to stop excessive bleeding. The cecum was exteriorized, and digital pressure was exerted to create subserosal hemorrhages over all cecal surfaces. The cecum was then returned to its normal anatomic position. The compound to be tested was placed in an Alzet miniosmotic pump to allow continuous release of the molecule throughout the postsurgical interval. The Alzet pump was placed in the subcutaneous space and a delivery tube connected the pump with the site of delivery (uterine horns of the rabbit). Vehicle was placed in the pump of control rabbits. The abdominal wall and skin were closed in a standardized manner.

After 7 days, the rabbits were sacrificed and the percentage of the area of the sidewall injury that is involved in adhesions was determined. In addition, the tenacity of the adhesion formed was scored using a 0+ to 3+ system as follows:

0=no adhesions

1=mild, easily disectable adhesions

2=moderate adhesions; non-disectable, does not tear organ

3=dense adhesions; non-disectable, tears the organ when removed.

A reduction in the area or the tenacity of the adhesions would be considered beneficial.

In additional experiments, a rabbit uterine horn model was employed. This model has been previously shown to cause severe adhesions in rabbits after surgery [Nishimura, K. et al., "The use of ibuprofen for the prevention of postoperative adhesions in rabbits," *Am. J. Med.* 77:102–6 (1984)]. The rabbits were anesthetized (130 mg/kg ketamine and 20 mg/kg acetylpromazine im) and prepared for sterile surgery. A midline laparotomy was performed, and surgical trauma was performed on both uterine horns by abrading the serosal surface with gauze until punctate bleeding developed. Ischemia of both uterine horns was induced by removal of the collateral blood supply. After traumatization, the abdominal wall was closed in two layers. The compound to be tested was delivered as described for the peritoneal sidewall model.

With the uterine horn model, an initial score (0 to 4+) to represent the overall extent of adhesions is given. The percentage of a surface of the horn involved in adhesions to various organs are given in the tables below the overall adhesion score.

Example 1

The efficacy of quinacrine in preventing adhesion formation was evaluated at two doses in the sidewall model. The vehicle was phosphate buffered saline (PBS). It was found that with both doses, some of the drug precipitated at the site of the tube. The precipitate appeared to be walled off. With the higher dose, one rabbit had precipitate on the cecum; with the lower dose, two rabbits had precipitate. The rabbits in the lower dose group with precipitate on the cecum also had extensive adhesion formation. Quinacrine was effective at reducing the area of adhesion formation.

| Treatment | % Adhesions | Adhesion Tenacity |
|---|---|---|
| Vehicle Control | 50 | 3+ |
|  | 100 | 3+ |
|  | 80 | 3+ |
|  | 40 | 2+ |
|  | 100 | 3+ |
|  | Infected |  |
| Mean area: | 74.0 |  |
| 5 mg/ml quinacrine | 0 | 0+ |
|  | 40 | 2+ |
|  | 80 | 1+ |
|  | Infected |  |
|  | 0 | 0+ |
|  | 40 | 1+ |
| Mean area: | 32.0 |  |
| 0.5 mg/ml Quinacrine | 80 | 3+ |
|  | 0 | 0+ |
|  | 100 | 2+ |
|  | 80 | 2+ |
|  | Died |  |
|  | 0 | 0+ |
| Mean area: | 52.0 |  |

Example 2

The procedure was repeated to confirm the efficacy of the 0.5 mg/ml dosage and determine if a lower dosage (0.167 mg/ml) was effective. Once again, with the 0.5 mg/ml dosage in some cases the quinacrine precipitated at the site of the tube; the precipitate appeared to be walled off, and one rabbit had precipitate on the cecum. With the 0.167 mg/ml dose, quinacrine precipitated at the site of the tube and the precipitate seemed to be walled off only in test animals exhibiting adhesions; in the animals with no adhesions, there was only a small amount of precipitate and it did not appear to be walled off.

| Treatment | % Adhesions | Adhesion Tenacity |
|---|---|---|
| Control | 90 | 2+ |
|  | 50 | 3+ |
|  | 80 | 3+ |
|  | 80 | 3+ |
|  | 90 | 2+ |
|  | 20 | 1+ |
| Mean area: | 68.3 |  |
| 0.5 mg/ml Quinacrine | 60 | 3+ |
|  | 50 | 3+ |
|  | 70 | 1+ |
|  | 0 | 0+ |
|  | 30 | 3+ |
|  | 80 | 3+ |
| Mean area: | 48.3 |  |
| 0.167 mg/ml Quinacrine | 0 | 0+ |
|  | 0 | 0+ |
|  | 70 | 1+ |
|  | 0 | 0+ |
|  | 10 | 1+ |
|  | 70 | 2+ |
| Mean area: | 25.0 |  |

Example 3

The effects of quinacrine at two dosage levels (0.167 mg/ml and 0.056 mg/ml) was examined in the double uterine horn model for adhesion prevention.

| Treatment | Overall Adhesion Score |
|---|---|
| Control | 2.5+ |
|  | 3.5+ |
|  | 3+ |
|  | 3+ |
|  | 3+ |
|  | 3.5+ |
| 0.167 mg/ml Quinacrine | 1.5+ |
|  | 1.5+ |
|  | 1+ |
|  | 2+ |
|  | 2+ |
|  | 2+ |
| 0.056 mg/ml Quinacrine | 1.5+ |
|  | 1.5+ |
|  | 1.5+ |
|  | 2+ |
|  | 1+ |
|  | 1+ |

| | % ORGAN INVOLVEMENT IN UTERINE HORN ADHESION | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| Control | 10 | 60 | 50 | 30 | 10 | 60 | 0 | 30 |
|  | 50* | 30 | 100 | 50 | 50 | 20 | 100 | 50 |
|  | 0 | 100 | 100 | 40 | 0 | 100 | 100 | 40 |
|  | 40 | 60 | 50 | 40 | 30 | 60 | 50 | 40 |
|  | 20** | 80 | 100 | 20 | 20 | 80 | 20 | 20 |

-continued

| | % ORGAN INVOLVEMENT IN UTERINE HORN ADHESION | | | | | | | |
|---|---|---|---|---|---|---|---|---|
| | Right Horn | | | | Left Horn | | | |
| Treatment | Bowel | Bladder | Itself | Left | Bowel | Bladder | Itself | Right |
| | 80* | 80 | 100 | 50 | 80 | 80 | 100 | 50 |
| Mean: | 33.3 | 68.3 | 83.3 | 38.3 | 31.7 | 66.7 | 61.7 | 38.3 |
| 0.167 Quinacrine | 0 | 0 | 60 | 40 | 0 | 0 | 60 | 40 |
| | 0 | 30 | 50 | 0 | 0 | 30 | 50 | 0 |
| | 10 | 0 | 0 | 20 | 10 | 0 | 0 | 20 |
| | 0 | 10 | 0 | 30 | 0 | 40 | 0 | 30 |
| | 40 | 50 | 40 | 0 | 40 | 50 | 40 | 0 |
| | 0 | 40 | 50 | 0 | 0 | 40 | 50 | 0 |
| Mean: | 8.3 | 21.6 | 33.3 | 15 | 8.3 | 26.7 | 33.3 | 15 |
| 0.056 Quinacrine | 10 | 20 | 0 | 0 | 10 | 10 | 50 | 0 |
| | 0 | 50 | 20 | 0 | 0 | 50 | 20 | 0 |
| | 10 | 10 | 40 | 0 | 10 | 0 | 40 | 0 |
| | 20 | 0 | 50 | 0 | 20 | 0 | 50 | 0 |
| | 0 | 10 | 30 | 0 | 0 | 10 | 30 | 0 |
| | 0 | 10 | 20 | 0 | 0 | 10 | 20 | 0 |
| Mean: | 6.7 | 16.7 | 26.7 | 0 | 6.7 | 13.3 | 35 | 0 |

*Approximately 80% of both horns involved with adhesions to the sidewall at the site of the tube
**Bowel adhered to the sidewall at the site of the tube

Example 4

The efficacy of quinacrine in the double uterine horn model was further evaluated in a kinetics study. In this study, the pump was disconnected at various times after surgery to determine the time period of exposure to the drug effective to reduce adhesion formation. The efficacy of quinacrine in preventing adhesion formation was most pronounced in this study. A few rabbits exhibited petechial hemorrhage or mechanical damage from tube placement.

| Treatment | Overall Adhesion Score |
|---|---|
| Vehicle | 2.5+ |
| | 3.5+ |
| | 3+ |
| | 3+ |
| | 3.5+ |
| | 3.5+ |
| 0.167 mg/ml Quinacrine/24 hr | 1.5+ |
| | 2+ |
| | 1.5+ |
| | 2+ |
| | 1+ |
| | 2+ |
| 0.167 mg/ml Quinacrine/48 hr | 2+ |
| | 1.5+ |
| | 2+ |
| | 1.5+ |
| | 2+ |
| | 1+ |
| 0.167 mg/ml Quinacrine/72 hr | 2.5+ |
| | 1.5+ |
| | 2+ |
| | 1.5+ |
| | 1.5+ |
| | 1.5+ |
| 0.056 mg/ml Quinacrine/24 hr | 3+ |
| | 1.5+ |
| | 1+ |
| | 0.5+ |
| | 1+ |
| | 1+ |
| 0.056 mg/ml Quinacrine/48 hr | 1.5+ |
| | 1+ |
| | 1+ |
| | 1.5+ |
| | 1.5+ |

-continued

| Treatment | Overall Adhesion Score |
|---|---|
| | 2+ |
| 0.056 mg/ml Quinacrine/72 hr | 2.5+ |
| | 1.5+ |
| | 1+ |
| | 1.5+ |
| | 2.5+ |
| | 1.5+ |

| Treatment | % ORGAN INVOLVEMENT IN UTERINE HORN ADHESION ||||||||
| | Right Horn |||| Left Horn ||||
| | Bowel | Bladder | Itself | Left | Bowel | Bladder | Itself | Right |
|---|---|---|---|---|---|---|---|---|
| Control | 40 | 20 | 50 | 0 | 40 | 20 | 50 | 0 |
| | 30 | 50 | 100 | 50 | 30 | 50 | 100 | 50* |
| | 30 | 50 | 50 | 40 | 40 | 50 | 50 | 40* |
| | 40 | 30 | 50 | 50 | 40 | 30 | 0 | 50* |
| | 50 | 70 | 60 | 40 | 50 | 70 | 60 | 40* |
| | 80 | 50 | 100 | 40 | 80 | 50 | 40 | 40 |
| Mean: | 45 | 40 | 68.3 | 36.7 | 45 | 40 | 50 | 36.7 |
| 0.167 Quinacrine/24 hr | 0 | 0 | 30 | 20 | 0 | 0 | 30 | 30* |
| | 20 | 20 | 30 | 50 | 0 | 20 | 30 | 50 |
| | 10 | 0 | 0 | 0 | 0 | 0 | 0 | 0* |
| | 0 | 40 | 20 | 10 | 0 | 40 | 20 | 10 |
| | 0 | 0 | 40 | 0 | 0 | 0 | 30 | 0 |
| | 20 | 0 | 10 | 0 | 20 | 0 | 40 | 0 |
| Mean: | 8.3 | 10 | 21.7 | 13.3 | 3.3 | 10 | 25 | 13.3 |
| 0.167 Quinacrine/48 hr | 40 | 0 | 50 | 0 | 40 | 0 | 50 | 0 |
| | 0 | 0 | 30 | 0 | 50 | 20 | 0 | 0* |
| | 50 | 0 | 10 | 30 | 50 | 0 | 0 | 30 |
| | 0 | 40 | 40 | 0 | 0 | 40 | 0 | 0 |
| | 40 | 0 | 0 | 10 | 40 | 0 | 10 | 10 |
| | 10 | 0 | 50 | 0 | 10 | 0 | 0 | 0 |
| Mean: | 23.3 | 6.7 | 30 | 6.7 | 31.7 | 10 | 10 | 6.7 |
| 0.167 Quinacrine/72 hr | 10 | 100 | 50 | 50 | 10 | 100 | 50 | 50 |
| | 0 | 30 | 20 | 30 | 0 | 30 | 20 | 30 |
| | 0 | 10 | 20 | 10 | 0 | 10 | 30 | 10 |
| | 0 | 20 | 0 | 10 | 0 | 20 | 0 | 10 |
| | 0 | 20 | 30 | 0 | 0 | 20 | 30 | 0* |
| | 0 | 0 | 70 | 0 | 0 | 0 | 20 | 0 |
| Mean: | 1.7 | 30 | 31.7 | 16.7 | 1.7 | 30 | 25 | 16.7 |
| 0.056 Quinacrine/24 hr | 50 | 20 | 50 | 50 | 50 | 20 | 50 | 50* |
| | 10 | 30 | 20 | 0 | 10 | 30 | 10 | 0 |
| | 0 | 0 | 50 | 20 | 0 | 0 | 20 | 20 |
| | 0 | 0 | 30 | 0 | 0 | 0 | 30 | 0 |
| | 10 | 0 | 0 | 0 | 10 | 0 | 20 | 0 |
| | 10 | 0 | 0 | 0 | 0 | 0 | 10 | 0 |
| Mean: | 13.3 | 8.3 | 25 | 11.7 | 11.7 | 8.3 | 23.3 | 11.7 |
| 0.056 Quinacrine/48 hr | 0 | 30 | 20 | 30 | 0 | 30 | 20 | 30 |
| | 10 | 20 | 20 | 0 | 0 | 20 | 0 | 0* |
| | 10 | 0 | 10 | 0 | 10 | 0 | 0 | 0* |
| | 0 | 0 | 20 | 10 | 0 | 0 | 0 | 10* |
| | 10 | 0 | 50 | 0 | 10 | 0 | 30 | 0 |
| | 0 | 0 | 40 | 30 | 0 | 0 | 40 | 30* |
| Mean: | 5 | 8.3 | 30 | 11.7 | 3.3 | 8.3 | 15 | 11.7 |
| 0.056 Quinacrine/72 hr | 20 | 30 | 50 | 20 | 20 | 30 | 50 | 20 |
| | 50 | 0 | 20 | 0 | 50 | 0 | 0 | 0 |
| | 0 | 0 | 50 | 0 | 0 | 0 | 40 | 0 |
| | 0 | 0 | 20 | 0 | 0 | 0 | 0 | 0* |
| | 30 | 30 | 20 | 10 | 30 | 30 | 20 | 10 |
| | 10 | 0 | 20 | 30 | 0 | 0 | 0 | 30 |
| Mean: | 18.3 | 10 | 30 | 10 | 16.7 | 10 | 18.3 | 10 |

*Right horn and/or bowel adhered to the sidewall (at either tube or tube suture); no inflammation observed at end of tube in these rabbits In summary, quinacrine has been shown to be effective in preventing the formation of adhesions in two animal models. Even if the drug is delivered by Alzet pump only for the first 24 hours after surgery, quinacrine was effective in reducing the formation of adhesions in a rabbit double uterine horn model.

While there have been shown and described the fundamental novel features of the invention, it will be understood that various omissions, substitutions and changes in the form and details illustrated may be made by those skilled in the art without departing from the spirit of the invention. It is the intention, therefore, to be limited only as indicated by the scope of the following claims.

What is claimed is:

1. A method for prevention in mammals of formation of adhesions between organ surfaces at a particular location, comprising:

administering quinacrine as active agent to provide an effective local concentration at the location for a period of time sufficient to permit tissue repair.

2. A method according to claim 1, wherein the period of time is about 24 hours to about 7 days after trauma to the location.

3. A method according to claim 1, wherein the active agent is administered in conjunction with a delivery vehicle which facilitates maintaining the effective local concentration of active agent.

4. A method according to claim 1, wherein the effective local concentration is between about 0.000001 µg/ml to about 28 mg/ml.

5. A method according to claim 4, wherein said effective local concentration is between about 0.0001 µg/ml to about 5 mg/ml.

6. A method according to claim 1, wherein the active agent is administered in the form of microcapsules or microspheres.

7. A method according to claim 6, wherein the microcapsules or microspheres comprise a biodegradable polymer selected from the group consisting of poly(dl-lactides), poly(dl-lactide-co-glycolides), polycaprolactones, polyglycolides, polylactic acid-co-glycolides, poly(hydroxybutyric acids), polyorthoesters, polyacetals and mixtures thereof.

8. A method according to claim 1, wherein the active agent is administered in the form of a lipid-based delivery system.

9. A method according to claim 8, wherein the lipid-based delivery system is selected from the group consisting of liposomes comprising L-alpha distearoyl phosphatidylcholine and extended-release formulations comprising spherical particles bounded by a single bilayer lipid membrane and each containing a plurality of nonconcentric aqueous chambers which encapsulate the active ingredient.

10. A method according to claim 1, wherein the active agent is administered as an intraperitoneal infusion.

11. A method according to claim 10, wherein the intraperitoneal infusion is administered by a miniosmotic pump.

12. A method according to claim 1, wherein the active agent is administered in the form of an instillate.

13. A method according to claim 12, wherein the instillate comprises a high-molecular-weight carrier selected from the group consisting of dextrans, cyclodextrans, hydrogels, carboxymethylcellulose, hyaluronic acid, chondroitin sulfate and mixtures thereof.

14. A method according to claim 1, wherein the active agent is administered in combination with an absorbable mechanical barrier.

15. A method according to claim 14, wherein the absorbable mechanical barrier comprises oxidized regenerated cellulose.

* * * * *